United States Patent [19]

Zaslavsky

[11] Patent Number: 5,734,024
[45] Date of Patent: Mar. 31, 1998

[54] METHOD FOR DETERMINING THE BIOLOGICAL ACTIVITY OF RECOMBINANT HUMAN GROWTH HORMONE

[75] Inventor: Boris Y. Zaslavsky, 7972 Burr Ridge Ct., #107, Woodridge, Ill. 60517

[73] Assignees: Boris Y. Zaslavsky, Woodridge, Ill.; Arnon Chait, Bay Village, Ohio

[21] Appl. No.: 635,384

[22] Filed: Apr. 19, 1996

[51] Int. Cl.$^6$ .............................. C07K 1/14; C07K 1/20; C07K 14/61
[52] U.S. Cl. .............. 530/412; 530/399; 530/417; 530/422
[58] Field of Search .......................... 530/399, 412, 530/422, 417

[56] References Cited

U.S. PATENT DOCUMENTS 5,407,810  4/1995  Builder et al. ...................... 435/69.1

OTHER PUBLICATIONS

Zaslavsky et al. Biochim. Biophys. Acta 579:463–465, 1979.
Wingun et al. J. Chromatog. B. 680:113–122, 1996.
Johansson, G. in Walter et al. (Ed) Partitioning in Aqueous Two–Phase Systems. Acad. Press, Orlando, FL. 161–226, 1985.
Zaslavsky, B.Y. Aqueous Two–Phase Partitioning. Marcel Dekker, Inc., New York. pp. 401–446, 1995.

*Primary Examiner*—John Ulm
*Assistant Examiner*—Christine Saoud
*Attorney, Agent, or Firm*—Fay, Sharpe, Beall, Fagan, Minnich & McKee

[57] ABSTRACT

A method is provided for determination of the biological activity, purity and/or homogeneity of recombinant human growth hormone ("rhGH") using an analytical chemistry test. The method is based on distribution of the rhGH between two or more immiscible aqueous phases and the subsequent determination of the ratio of rhGH concentration in the phases. The ratio is then used as a relative measure of biological activity, homogeneity, and purity, when calibrated against a sample of rhGH that was previously characterized with respect to its activity, homogeneity and purity. Typical applications of this test include quality control, quality assurance, biological identity testing, etc.

16 Claims, 1 Drawing Sheet

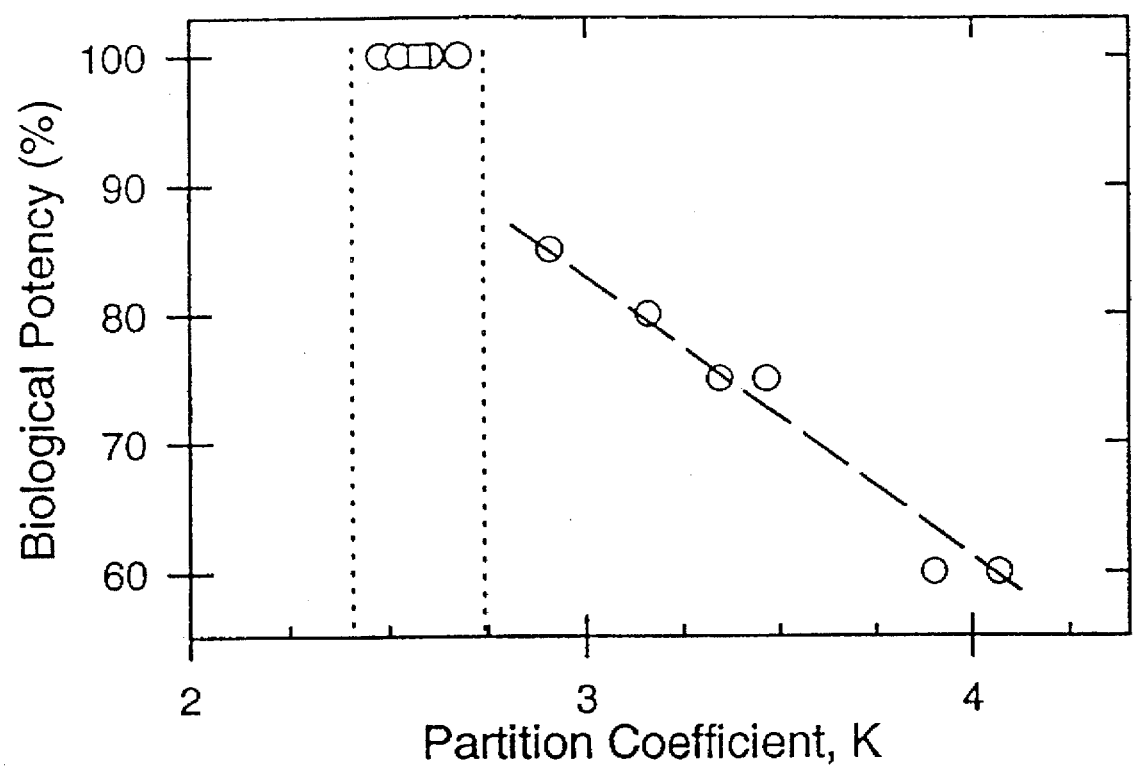

METHOD FOR DETERMINING THE BIOLOGICAL ACTIVITY OF RECOMBINANT HUMAN GROWTH HORMONE

FIELD OF INVENTION

This invention is directed to a method for assessing the biological activity level and purity, and homogeneity of recombinant human growth hormone (rhGH). In addition, the method of the present invention can be utilized for the characterization and quality control of human growth hormone produced by recombinant DNA (rDNA) technology.

BACKGROUND OF THE INVENTION

Recombinant DNA (rDNA) technology has led to the development of new protein-based drugs that are gaining worldwide regulatory approval. Human growth hormone, human insulin, β- and γ-interferons, and erythropoietin are just a few examples of approved rDNA-derived biopharmaceuticals.

The biological effects, purity, and potency of a drug is governed by the chemical structure of the drug for both traditional drugs and biopharmaceuticals. Standard analytical methodologies used for structural analysis of conventional drugs are, however, inadequate for complete characterization of protein-based products.

Two main reasons for this inadequacy are the large molecular size and conformational flexibility of protein-based drugs. The large molecular size hinders the possibility to detect, for example, replacement or chemical modification of a single amino acid residue or a change in a single glycosylation site. These alterations of the biomolecule structure, however, may lead to subtle changes of the molecule conformation resulting in significant changes in the pharmacological properties of the product.

Additionally, the wrong choice of manufacturing conditions or formulation may lead to improperly folded polypeptide chains which are biologically inactive. Hence, further methodologies capable of analysis of the protein conformation are needed.

Currently, the analysis of biopharmaceuticals relies heavily on the use of sophisticated methods for the demonstration of the structural identity, homogeneity and purity of the products. These methods include amino acid and carbohydrate analysis, N- and C-terminal sequence analysis, spectroscopic (UV, CD, ORD) analysis, peptide mapping, electrophoresis, chromatographic purity profile methods, potency/activity assays, etc. It must be emphasized that no one method is considered to be sufficient in itself, and that multiple methods are necessary to completely characterize and/or control such products.

For example, amino acid analysis for proteins with molecular weights above about 16 kilodaltons is known to be of very limited value. While useful for identification of the target protein, N-terminal and C-terminal sequencing only partially characterize the protein. Analysis of the primary structure, however, is insufficient to assure the biological potency of a protein, particularly since the potency depends on the protein conformation.

The conformation of proteins is usually analyzed by optical spectroscopy, such as UV spectroscopy, fluorescence spectroscopy, optical rotary dispersion, or circular dichroism. These methods are generally not sensitive enough to detect the subtle conformational changes caused by small alterations in the protein structure, especially if these changes do not affect side-chain chromophores from tryptophan, phenylalanine, tyrosine, and cysteine residues within the protein. Furthermore, these methods as well as others, such as electrophoresis, isoelectric focusing, differential scanning calorimetry, light scattering, ultracentrifugation, gel filtration, and immunological assays, only provide information about a particular structural or functional feature of a protein.

Chromatography is currently the most widely used analytical method for determining the purity of small organic drugs. Four modes of High-Performance Liquid Chromatography (HPLC) currently used for protein analysis are size-exclusion, ion-exchange, reversed-phase, and hydrophobic interaction chromatography. All these HPLC methods, though commonly employed to monitor the purity of biopharmaceuticals, are usually incapable of resolving proteins that differ by one or two residues or detecting other small changes in the macromolecular structure.

Hence, while chromatography is sufficient for determining whether a small organic drug is functional, the evaluation of a biopharmaceutical requires measurements of biological activity. Many of these measurements are the animal-based assays, particularly when the mechanism of action of the biopharmaceutical is not well defined. These assays are generally imprecise (with variability often 30% to 100%), time-consuming, and costly, and are not rugged. Cell culture assays can be used when the protein-based drug produces a measurable response in a cell-based system. The variability of these assays is much lower, often in the range of 10% to 30% or better (e.g., in vitro clot lysis assay has a variability of about 5%).

Physicochemical tests are much faster, more precise, and more reliable than biological assays. A physicochemical test providing information related to the biological potency of a protein-based drug would improve the control of the safety and efficacy of the drug.

Such a test should meet the following requirements: (1) it should provide information quantitatively related to the biological potency of a biopharmaceutical, (2) it should be capable of detecting minor changes in the structure of large macromolecules, (3) it should be especially sensitive to the structural changes affecting the efficacy of a biomacromolecule, (4) it should be sensitive to the presence of impurities in the product in quantities as small as 0.1 to 0.01 wt. %, (5) it should be simple, precise, and rugged, and (6) it should be time-, labor-, and cost-effective so as not to increase the overall cost of the product. Even if only some of these requirements were met, the test would improve the possibilities for assuring the safety and efficacy of biopharmaceuticals, such as recombinant human growth hormone (rhGH).

Thus, it is the object of the present invention to provide improved method for determining the biological activity, homogeneity, and purity of rhGH. This and other objects of the invention will become apparent in view of the detailed description below.

BRIEF DESCRIPTION OF THE DRAWINGS

The following is a brief description of the drawings which are presented for the purpose of illustrating the invention and not for the purposes of limiting the same.

The FIGURE illustrates the relationship between the partition coefficient and biological potency (in percent) for commercial samples of recombinant human growth hormone preparations. Square symbol represents reference sample; dotted lines indicate the K-range for samples with 100% biological potency.

SUMMARY OF THE INVENTION

The present invention is directed to a process of determining the biological activity, purity and/or homogeneity of recombinant human growth hormone ("rhGH") using an analytical physicochemical test. The method is based on distribution of the rhGH between two or more immiscible aqueous phases and the subsequent determination of the ratio of rhGH concentration in the phases. The ratio is then used as a relative measure of biological activity, homogeneity, and purity of the sample, when calibrated against a sample of rhGH that was previously characterized with respect to its activity, homogeneity and purity. Typical applications of said test include quality control, quality assurance, biological identity testing, etc.

DETAILED DESCRIPTION OF THE INVENTION

Partitioning in aqueous polymer multi-phase systems is a highly efficient, versatile, and cost-effective method for characterizing rhGH. Aqueous two-phase systems arise in aqueous mixtures of different water-soluble polymers or a single polymer and a specific salt. When two certain polymers, e.g., dextran and polyethylene glycol ("PEG"), are mixed in water above certain concentrations, the mixture separates into two immiscible aqueous phases. A clear interfacial boundary develops; one phase is rich in one polymer and the other phase is rich in the other. The aqueous solvent in both phases provides media suitable for biological products such as rhGH.

By choosing the type and concentration of phase-forming polymers, the properties of the phases can be varied. Additionally, the composition of the phases and their properties may be changed by adding inorganic salts and/or organic solvents. Examples of such aqueous polymer two-phase systems useful in the characteristic of rhGH include, but are not limited to, dextran/PEG, dextran/PVP, PEG/salt, PVP/salt, etc.

When a solute such as rhGH is put into such a system, it distributes between the two phases. The procedure is fairly simple and similar to extraction. Solutions of two polymers are mixed and a two-phase system is formed. Centrifugation to speed phase settling may be used to enhance separation. Partition behavior of rhGH may be influenced by many variables, such as pH, polymer and salt compositions of the system, temperature, etc.

Partitioning of a solute such as rhGH is characterized by the partition coefficient, "K", defined as the ratio between the concentrations of the solute in the two immiscible phases at equilibrium. For example, the partition coefficient, K, of rhGH is defined as the ratio of rhGH in first phase to that of the second phase in a biphasic system.

It has been determined that the partition coefficient K of rhGH in certain two-phase aqueous systems can provide a highly sensitive measure for changes in the biological activity, purity, and homogeneity of the product.

In order to determine the partition coefficient K of a sample of rhGH to be analyzed, concentrated stock solutions of all the components (polymer 1, e.g., Dextran; polymer 2, e.g., PEG; salts, etc.) in water are prepared separately. The stock solutions of phase polymers, salts, and rhGH are mixed in the amounts and conditions (i.e., pH from about 4.5 to about 8.5, temperature from about 4° C. to 60° C., salt concentration from about 0.01 to 1 mol/kg) appropriate to bring the system to the desired composition and vigorously shaken. Then the system can be allowed to equilibrate, or it can be centrifuged for 10–20 minutes at about 4400 g or higher to speed phase settling. Aliquots of the settled phases are pipetted from both the top and bottom phases and analyzed for the concentrations of rhGH.

Different assay methods may be used to determine the concentration of rhGH in each phase. The most common peptide or protein detection techniques include direct spectrophotometry and dye binding reactions with Coomassie Blue G-250 or fluorescamine. The concentration of rhGH in each phase is then utilized to determine the partition coefficient, K, of the sample. This number is then compared with known partition coefficient (K) values to determine the biological activity of the sample.

The present invention is further illustrated by the following detailed examples. It is to be understood that the invention is not limited to the specific examples, and various changes and modifications may be made in the invention without departing from the spirit and scope thereof.

Partitioning of samples from 10 different lots of the commercially available therapeutic recombinant human growth hormone (somatotropin) preparation was examined in an aqueous Dextran/Polyvinyl pyrrolidone two-phase system containing sodium sulfate as an additive. Zaslavsky, B. Y., "Aqueous Two-Phase Partitioning: Physical Chemistry and Bioanalytical Applications," Marcel Dekker, New York, 1994.

The aqueous two-phase systems contained 11.0 wt. % Dextran, 12.0 wt. % Polyvinylpyrrolidone, and 0.10 mole/kg $Na_2SO_4$ in 0.01 mole/kg sodium phosphate buffer (pH 7.4) were prepared as described previously. Zaslavsky, B. Y., Mestechkina, N. M., and Rogozhin, S. V., "Relative Hydrophobicity of Human Serum Proteins as Measured by Partition in Aqueous Two-Polymer Phase Systems," Biochimica et Biophysica Acta, Vol. 579, No. 2, 1979, pp 463–465. By mixing appropriate amounts of polymer and salt/buffer stock solutions a partition system with a total weight of about 2 g was prepared. The two phases of the system were of equal volume. Solutions of growth hormone preparations (in 2% w/v glycine, 0.25% w/v sodium bicarbonate, 0.2% w/v mannitol, 0.2% w/v lactose) containing about 1 mg growth hormone were added to the aqueous partition system. The liquid/liquid system was shaken and then centrifuged for 10 to 15 minutes at 4400 g to speed phase settling. Aliquots of the settled phases were removed by pipette for further analysis.

The concentration of the hormone in each phase were determined using dye binding reaction with Coomassie Blue G-250. The partition coefficient for each hormone sample represents the mean of two to three measurements on 4 to 5 dilutions from each partition experiment. The partition experiments were carried out in duplicate or triplicate. Deviation from the mean K value did not exceed ±3% in all the cases.

Biological potency for each sample was measured by in-vivo bioassay using the hypophysectomized rat weight gain as described in European Pharmacopoeia 1987, 2nd Ed., Par. II, FSC, 11, 556. The potency for highly purified native somatotropin (reference sample) obtained from Sigma Chemical Co., St. Louis, was taken as 100%.

The partition coefficients of the samples were compared to that of the reference sample (K=2.58±0.12). They varied from 2.48 to 4.07. No correlation between the K-values and electrophoretic purity, monomer content, or results of the radioimmunoassay analysis could be found.

The relationship observed between the partition coefficient of a hormone sample and its biological potency is shown in the FIGURE. The day-to-day reproducibility of the partition coefficient values for two randomly selected separate samples was better than 4%, and the analyst-to-analyst variability did not exceed 5%. The partition technique was found to be much more sensitive and more time- and cost-effective than other methodologies currently used to analyze the therapeutic recombinant human growth hormone preparations. Bristow, A. F., and Jeffcoate, S. L., "Analysis of Therapeutic Growth Hormone Preparations: Report of an Interlaboratory Collaborative Study on Growth Hormone Assay Methodologies," Biologicals, Vol. 20, No. 2, 1992, pp 221–231. Thus, the suggested quality control test consists of determining if the partition coefficient value for the product being analyzed is in the range specific for the reference sample.

The above results demonstrate that the aqueous two-phase partition technique can be used as a highly sensitive reliable, simple, and inexpensive method for analysis and quality control of recombinant products such as rhGH and other biological materials. The data indicates that the partition coefficient of a biological solute such as rhGH is related to the biological potency of the solute. Accordingly, the partition technique of the present invention may be used as a bioanalytical method for characterization, quality control, and assessment of the lot-to-lot consistency of recombinant products such as rhGH.

The invention has been described with reference to the preferred embodiment. Obviously, modifications and alterations will occur to others upon a reading and understanding of the preceding detailed description. It is intended that the invention be construed as including all such alterations and modifications insofar as they come within the scope of the appended claims or the equivalents thereof.

Having thus described the invention, it is claimed:

1. A method for characterizing the biological activity of a sample of recombinant human growth hormone (rhGH) comprising the steps of:
   a) forming an aqueous polymer multiphase system capable of separation into two or more immiscible phases wherein the system is designed to be sensitive to structural changes in a protein affecting the efficacy of the protein;
   b) mixing a sample consisting of rhGH to be characterized with the system;
   c) maintaining the system until phase separation occurs;
   d) analyzing the concentrations of rhGH in the separated phases;
   e) determining the partition coefficient (K) defined as the ratio between the concentrations of rhGH in the phases; and
   f) comparing the determined partition coefficient (K) of rhGH with a range of known partition coefficients of rhGH which are indicative of acceptable biological activity for a sample of rhGH thereby assessing the biological activity of the sample of rhGH characterization.

2. The method of claim 1, wherein the pH in the phases is within the range of pH from 4.5 to 8.5.

3. The method of claim 1, wherein the total amount of rhGH does not exceed 10 % wt. of the total system weight.

4. The method of claim 1, wherein the temperature of the system is in the range of 4° C. to 60° C.

5. The method of claim 1, wherein the composition of the system provides a quantitative relationship between the partition coefficient (K) and biological potency of the product sample.

6. The method of claim 1, wherein the partition coefficient (K) of a sample of rhGH with 100% biological potency, activity, and purity displays the partition coefficient (K) value equal or less than 0.90 or equal or more than 1.1.

7. The method of claim 1, wherein the partition coefficient (K) is measured for a sample of a given product in two or more aqueous two-phase systems of different compositions selected from the group consisting of a polymer/polymer system and a polymer/salt system.

8. The method of claim 1, wherein the partition coefficient (K) of a product in a given aqueous two-phase system is to be measured as a function of the total concentration of the product in the system in order to increase the precision of the partition coefficient (K) value.

9. The method of claim 1, wherein the system used for partitioning of rhGH is calibrated with partition coefficients (K) for a specifically selected set of low and high molecular weight compounds in addition to the reference sample of rhGH.

10. The method of claim 7, wherein said polymer/polymer system is dextran/polyethylene glycol.

11. The method of claim 7, wherein said polymer/polymer system is dextran/polyvinyl pyrrolidone.

12. The method of claim 7, wherein said polymer/salt system is polyethylene glycol/$Na_2SO_4$.

13. The method of claim 7, wherein said polymer/salt system is polyvinyl pyrrolidone/$K_2HPO_4$.

14. A method for characterizing the biological activity of a sample of recombinant human growth hormone (rhGH) comprising the steps of:
   a) mixing a sample consisting of rhGH to be characterized with an aqueous dextran/polyvinylpyrrolidone two-phase system wherein the system is designed to be sensitive to structural changes in a protein affecting the efficacy of the protein;
   b) maintaining the system until phase separation occurs;
   c) analyzing the amount of rhGH in the separated phases;
   d) determining the partition coefficient (K) of rhGH in the two-phase system; and,
   e) comparing the partition coefficient (K) of the rhGH sample with a range of known partition coefficients (K) of a reference rhGH which are indicative of acceptable biological activity for a sample of rhGH thereby determining the biological activity of the sample of rhGH being characterized.

15. A method for characterizing the biological activity of a sample of recombinant human growth hormone (rhGH) comprising the steps of:
   forming an aqueous polymer multiphase system capable of separation into two or more immiscible phases wherein the system is designed to be sensitive to changes in protein structure related to biological activity while minimizing the effect on the partition coefficient (K) resulting from mutations;
   b) mixing a sample of rhGH to be characterized with the system wherein the sample is devoid of any extraneous protein material other than rhGH;
   c) maintaining the system until phase separation occurs;
   d) analyzing the concentrations of rhGH in the separated phases;
   e) determining the partition coefficient (K) defined as the ratio between the concentrations of rhGH in the phases; and
   f) comparing the determined partition coefficient (K) of rhGH with a range of known partition coefficients of rhGH which are indicative of acceptable biological activity for the sample of rhGH thereby assessing the biological activity of the sample of rhGH being characterized.

16. A method for characterizing the biological activity of a sample of recombinant human growth hormone (rhGH) comprising the steps of:
   a) forming an aqueous polymer multiphase system capable of separation into two or more immiscible phases wherein the system is designed to be sensitive to changes in protein structure related to biological activity while minimizing the effect on the partition coefficient (K) resulting from mutations;
   b) miming a sample consisting of rhGH to be characterized with the system;
   c) maintaining the system until phase separation occurs;
   d) analyzing the concentrations of rhGH in the separated phases;
   e) determining the partition coefficient (K) defined as the ratio between the concentrations of rhGH in the phases; and
   f) comparing the determined partition coefficient (K) of rhGH with a range of known partition coefficients of rhGH which are indicative of acceptable biological activity for a sample of rhGH thereby assessing the biological activity of the sample of rhGH being characterized.

* * * * *